(12) United States Patent
Xia (10) Patent No.: US 9,434,955 B2
(45) Date of Patent: Sep. 6, 2016

(54) PROTEINS RELATING TO GRAIN SHAPE AND LEAF SHAPE OF RICE, CODING GENES AND USES THEREOF

(75) Inventor: Xinjie Xia, Changsha (CN)

(73) Assignee: INSTITUTE OF SUBTROPICAL AGRICULTURE, CHINESE ACAD, Hunan, Changsha (CN)

( * ) Notice: Subject to any disclaimer, the term of this patent is extended or adjusted under 35 U.S.C. 154(b) by 797 days.

(21) Appl. No.: 13/391,993

(22) PCT Filed: Jul. 8, 2010

(86) PCT No.: PCT/CN2010/001015
§ 371 (c)(1),
(2), (4) Date: May 23, 2012

(87) PCT Pub. No.: WO2011/022930
PCT Pub. Date: Mar. 3, 2011

(65) Prior Publication Data
US 2012/0240292 A1    Sep. 20, 2012

(30) Foreign Application Priority Data
Aug. 24, 2009  (CN) .......................... 2009 1 0091728

(51) Int. Cl.
*A01H 5/10*   (2006.01)
*C12N 15/82*  (2006.01)
*C12N 15/29*  (2006.01)
*C07K 14/415* (2006.01)

(52) U.S. Cl.
CPC ......... *C12N 15/8261* (2013.01); *C07K 14/415* (2013.01)

(58) Field of Classification Search
None
See application file for complete search history.

(56) References Cited

U.S. PATENT DOCUMENTS

2004/0123343 A1* 6/2004 La Rosa et al. ............. 800/278
2004/0219675 A1 11/2004 Sainz et al.

FOREIGN PATENT DOCUMENTS

CN    101161675    4/2008

OTHER PUBLICATIONS

Hussain et al. (J Virol. Apr. 2005; 79(7): 4434-4439).*
Kant et al. (Biologia Plantarum 51 (1): 61-68, 2007).*
GenBank Accession No. NM_001052345, Feb. 14, 2008, retrieved from http://www.ncbi.nlm.nih.gov/nuccore/115444060., 5 pages.
International Search Report dated Oct. 8, 2010 issued to priority international application No. PCT/CN2010/001015.

* cited by examiner

Primary Examiner — Anne Kubelik
Assistant Examiner — Charles Logsdon
(74) Attorney, Agent, or Firm — Knobbe Martens Olson & Bear, LLP (57) ABSTRACT

The present invention provides a protein OsXCL relating to grain shape and leaf shape of rice, its derived proteins and their coding genes. Transgenic rices over-expressing OsXCL gene present phenotypes as increase of grain length, grain weight and number of grains per panicle, and leaf rolling and so on. The present invention also provides the method for obtaining transgenic plants by transforming the coding genes of OsXCL or its derived proteins into objective plants.

9 Claims, 8 Drawing Sheets

OsXCL transgenic 9311    Empty vector 9311 control

```
                          SEQUENCE LISTING

<160> NUMBER OF SEQ ID NOS: 13

<210> SEQ ID NO 1
<211> LENGTH: 1062
<212> TYPE: DNA
<213> ORGANISM: Oryza sativa

<400> SEQUENCE: 1
ctcacacacc acaccacacc aacatcgagc gcgtcgagtc gaatccaatc cactccactc     60
caccccgcga tctcctctcc tctcgtctcc ggcgaagacg acgtgatgcc acccagcgcc    120
gccgccgcag ccgcgatggc gcagtcgccg cgcagcctcc acacgctgat cagcttcggc    180
cgcggcgccg acggcgtcga cgacgatgag gccacgcccg cgtcggtcga cgttggtgac    240
gcggagggcg ccgggctcga cctcgacttc gcgttcgcgc cgccggtgtc ggcggccgag    300
ctggcgccgg ccgacgacat cttcgcgcac ggccgcatcg tgccggcgta cccggtgttc    360
gaccgcagcc tcctcgacct ctcgcccggc gacgcctcca cggcggcgcc ctccgccgac    420
acctactgcg cgtggacgcc gcgctcggcg ccgggctcgc ccggccgcga caggttcccc    480
aagagcgcgt ccaccggcgg agagtcgtcg tcgtcatcgc ggcgctggcg cctgcgcgac    540
ctcgtcggcg ccggcggccg ctcccgcagc gacggcaagg acaagttcgc cttcctgcac    600
caccacgccg ccgcgccgcc atcatccaaa ctgaagactc ctcctccccc tcaacaacca    660
cagcagaaga agcagagcgc cgtgaagacg aagccggcgg cgaagaaggg cgtggtcacc    720
gagatggaca tggccaccgc gcacaggctc ttctacagca aggccagcgc cggcggcgac    780
cggcggccgc agcaagcctc gtacctgacg taccgaccgg cgttcagcgg cctcttcgcg    840
ctcggccggt cgcaacacca caccgcctat tagtttaatc acttggtcaa taaccaaacc    900
aactgattac tagtggtagt tgttgttaaa ttaattgttt tgttgtaaaa gtgttcaaaa    960
ttttcggcga aattcgagtc gagatttctc gtttgtacta gaaccttatc atgtacataa   1020
atggaaaaag agaggaatga aatttgagag atgattttgt ct                      1062

<210> SEQ ID NO 2
<211> LENGTH: 255
<212> TYPE: PRT
<213> ORGANISM: Oryza sativa

<400> SEQUENCE: 2

Met Pro Pro Ser Ala Ala Ala Ala Ala Met Ala Gln Ser Pro Arg
1               5                   10                  15

Ser Leu His Thr Leu Ile Ser Phe Gly Arg Gly Ala Asp Gly Val Asp
                20                  25                  30

Asp Asp Glu Ala Thr Pro Ala Ser Val Asp Val Gly Ala Glu Gly
            35                  40                  45

Ala Gly Leu Asp Leu Asp Phe Ala Phe Ala Pro Pro Val Ser Ala Ala
        50                  55                  60

Glu Leu Ala Pro Ala Asp Asp Ile Phe Ala His Gly Arg Ile Val Pro
65                  70                  75                  80

Ala Tyr Pro Val Phe Asp Arg Ser Leu Leu Asp Leu Ser Pro Gly Asp
                85                  90                  95
```

```
Ala Ser Thr Ala Ala Pro Ser Ala Asp Thr Tyr Cys Ala Trp Thr Pro
            100                 105                 110

Arg Ser Ala Pro Gly Ser Pro Gly Arg Asp Arg Phe Pro Lys Ser Ala
        115                 120                 125

Ser Thr Gly Gly Glu Ser Ser Ser Ser Arg Arg Trp Arg Leu Arg
    130                 135                 140

Asp Leu Val Gly Ala Gly Gly Arg Ser Arg Ser Asp Gly Lys Asp Lys
145                 150                 155                 160

Phe Ala Phe Leu His His His Ala Ala Pro Pro Ser Ser Lys Leu
                165                 170                 175

Lys Thr Pro Pro Pro Gln Gln Pro Gln Gln Lys Lys Gln Ser Ala
            180                 185                 190

Val Lys Thr Lys Pro Ala Ala Lys Lys Gly Val Val Thr Glu Met Asp
        195                 200                 205

Met Ala Thr Ala His Arg Leu Phe Tyr Ser Lys Ala Ser Ala Gly Gly
            210                 215                 220

Asp Arg Arg Pro Gln Gln Ala Ser Tyr Leu Thr Tyr Arg Pro Ala Phe
225                 230                 235                 240

Ser Gly Leu Phe Ala Leu Gly Arg Ser Gln His His Thr Ala Tyr
                245                 250                 255

<210> SEQ ID NO 3
<211> LENGTH: 5
<212> TYPE: PRT
<213> ORGANISM: Artificial Sequence
<220> FEATURE:
<223> OTHER INFORMATION: Protein tag

<400> SEQUENCE: 3

Arg Arg Arg Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Protein tag

<400> SEQUENCE: 4

His His His His His His
1               5

<210> SEQ ID NO 5
<211> LENGTH: 8
<212> TYPE: PRT
<213> ORGANISM: Artificial Sequence
<220> FEATURE:
<223> OTHER INFORMATION: Protein tag

<400> SEQUENCE: 5

Asp Tyr Lys Asp Asp Asp Asp Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Protein tag

<400> SEQUENCE: 6
```

Trp Ser His Pro Gln Phe Glu Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Protein tag

<400> SEQUENCE: 7

Glu Gln Lys Leu Ile Ser Glu Glu Asp Leu
1               5                   10

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ccatgggaat ccaatccact ccactccacc                                   30

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
ggatccctaa taggcggtgt ggtgttgcg                                    29

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
acctgcctga aaccgaactg                                              20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ctgctccata caagccaacc                                              20

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
ccgccatcat ccaaactga                                               19

<210> SEQ ID NO 13
<211> LENGTH: 19

```
<212> TYPE: DNA
<213> ORGANISM: Artificial Sequence
<220> FEATURE:
<223> OTHER INFORMATION: primer

<400> SEQUENCE: 13
ggtgaccacg cccttcttc                                               19
```

PROTEINS RELATING TO GRAIN SHAPE AND LEAF SHAPE OF RICE, CODING GENES AND USES THEREOF

CROSS-REFERENCE TO RELATED APPLICATIONS

This application is the U.S. National Phase under 35 U.S.C. §371 of International Application PCT/CN2010/001015, filed Jul. 8, 2010, which was published in a non-English language, which claims priority to CN 200910091728.9, filed Aug. 24, 2009.

FIELD OF THE INVENTION

The present invention relates to the field of biotechnology, particularly, to grain length, grain weight, grain number per panicle and rolled leaf-related protein in rice, encoding gene thereof and use of the same.

DESCRIPTION OF BACKGROUND

Rice is one of the main grain crops on which the life of human being depends, provides staple food for nearly one half of the world population. In China, rice stands first among all grain crops in production and accounts for 60% of grain ration consumption of Chinese residents; nearly half of the farmers are engaged in rice production. Accordingly, rice plays a leading role in Chinese food crops. With the increasing growth of global population (the population growth rate of rice-consuming countries is faster than the average growth rate of the world population) and rapid development of industrialization and urbanization as well as damages caused by natural disasters and the like, there is an decreasing trend in rice paddies, causing a pressing conflict between the global rice supply and demand. How to produce more food on less rice paddy lands so as to ensure the safe supply of rice? It is an urgent problem we are facing and must overcome. However, the rice output under large-scale production is generally very low. According to an investigation conducted by the Food and Agriculture Organization of the United Nations (FAO) in 1999, the world average rice yield per unit area is only 3.8 t·ha-1 (6.3 t·ha-1 in China). For this end, China has put forward the rice breeding project for super high yield (the super rice breeding project) in recent 30 years to develop the yield potential of high yield varieties and thereby, substantially improving the rice yield. Grain weight and grain number per panicle are important factors affecting crop production, and increasing grain size, grain weight or grain number per panicle is an effective approach to improve rice yield. Moreover, the length of grain is an important morphological character that decides the rice quality. As to the biologists and agronomists, it is a goal most worth pursuing to raise both production and quality of rice.

DISCLOSURE OF THE INVENTION

An object of the present invention is to provide a protein from rice, designated as OsXCL, which is the protein of the following 1) or 2):
1) a protein, consisting of amino acid sequence as set forth by SEQ ID NO. 2 in the Sequence Listing;
2) a protein, derived from 1) by subjecting the amino acid sequence of SEQ ID NO. 2 in the Sequence Listing to substitution and/or deletion and/or addition of one or more amino acids, which is related to the grain length, grain weight, grain number per panicle and leaf shape of plant.

SEQ ID NO. 2 is an amino acid sequence of OsXCL comprising 255 amino acids, wherein there are 72 hydrophobic amino acids (including proline), 183 hydrophilic amino acids, 34 acidic amino acids and 38 basic amino acids. The protein has a molecular weight of 26.73 Kda and an isoelectric point of 9.8. It is a new protein that has not been reported.

A tag as set forth in Table 1 may be linked to an amino terminal or carboxyl terminal of the protein consisting of amino acid sequence set forth by SEQ ID NO. 2 in the Sequence Listing for convenient purification of OsXCL in 1).

TABLE 1

Sequence of Tags

| Tags | Residues | Sequence | SEQ ID NO: |
|---|---|---|---|
| Poly-Arg | 5-6 (typically, 5) | RRRRR | 3 |
| Poly-His | 2-10 (typically, 6) | HHHHHH | 4 |
| FLAG | 8 | DYKDDDDK | 5 |
| Strep-tag II | 8 | WSHPQFEK | 6 |
| c-myc | 10 | EQKLISEEDL | 7 |

The OsXCL in the above 2) may be obtained by artifical synthesization, or may be obtained by synthesizing the encoding gene thereof prior to biological expressing. The encoding gene of OsXCL of the above 2) may be obtained by subjecting the DNA sequence as set forth by the bases from positions 106 to 870 staring from the 5' end of SEQ ID NO. 1 in the Sequence Listing to deletion of codons of one or more amino acid residues, and/or subjecting one or more base pairs to missense mutation, and/or linking the encoding sequence of a tag as set forth in Table 1 at the 5' terminal and/or 3' terminal thereof.

The encoding gene of the above protein, designated as OsXCL, also falls into the protection scope of the present invention.

The above encoding gene is a gene of the following 1) or 2) or 3) or 4):
1) a gene, having an encoding sequence as set forth by positions 106-870 from the 5' end of SEQ ID NO. 1 in the Sequence Listing;
2) a gene, having an encoding sequence as set forth by positions 50-873 from the 5' end of SEQ ID NO. 1 in the Sequence Listing;
3) a gene, hybridizing with the gene defined in 1) or 2) under high stringency conditions and encoding said protein;
4) a gene, exhibiting 80%, or more than 80% homology to the gene defined in 1) or 2) and encoding said protein.

SEQ ID NO. 1 is an OsXCL-encoding full length cDNA consisting of 1062 bases, wherein, the 5' non-translational region comprises 105 bases, the 3' non-translational region comprises 192 bases, and the coding region comprises 765 bases (from position 106 to position 870), which encodes the OsXCL protein having the amino acid sequence of SEQ ID NO. 2 in the Sequence Listing. In coding region, A comprises 15.16% (116), C comprises 40.65% (311), G comprises 32.29%, (247), T comprises 11.9% (91), A+T comprises 27.06% (207), and C+G comprises 72.94% (558).

The above high stringency condition is: placing the hybrid film in a pre-hybridization solution (0.25 mol/L sodium phosphate buffer solution, pH 7.2, 7% SDS) for pre-hybridizing at 65° for 30 min; removing the pre-hybridization solution, and adding a hybridization solution (0.25 mol/L sodium phosphate buffer solution, pH 7.2, 7% SDS, isotope-labeled nucleotide fragment) for hybridizing at 65° for 12 hr; removing the hybridization solution, and adding a membrane cleaning solution I (20 mmol/L sodium phosphate buffer solution, pH 7.2, 5% SDS), washing the membrane at 65° twice, each lasting for 30 min; adding a membrane cleaning solution II (20 mmol/L sodium phosphate buffer solution, pH 7.2, 1% SDS), washing the membrane at 65° for 30 min.

The primer pairs used for amplifying the full-length of the above OsXCL gene or any fragment thereof also fall into the protection scope of the present invention.

The transgenic cell line containing the above gene also falls into the protection scope of the present invention.

The recombinant strain containing the above gene also falls into the protection scope of the present invention.

The recombinant vector containing the above gene also falls into the protection scope of the present invention.

The recombinant expression vector containing the OsXCL gene may be constructed with existing plant expression vectors. The plant expression vectors include binary *Agrobacterium* vetors and vectors that can be used in plant microprojectile bombardment and the like, such as pCAMBIA3301, pCAMBIA1300, pBI121, pBin19, pCAMBIA2301, pCAMBIA1301-UbiN, pBY505 or other derived plant expression vector. When constructing a recombinant expression vector with OsXCL gene, any of the enhancement promoter, constitutive promoter, tissue specific promoter or inducible promoter which can be used alone or in combination with other plant promoters, such as cauliflower mosaic virus (CAMV) 35S promoter, ubiquitin gene promoters (pUbi), Actin promoter and the like may be added before the transcription initiation nucleotide thereof.

In addition, when constructing a plant expression vector with the gene of the present invention, an enhancer including translational enhancer or transcription enhancer may also be used. These enhancer regions may be ATG start codons or start codons of adjacent regions and the like, which must be identical with the reading frame of a coding sequence to guarantee correct translation of the whole sequence. There are abundant sources for the translation regulatory signal and start codon, which may be natural-occurring or synthesized. A translation initiation region may be from a transcription initiation region or a structural gene.

The plant expression vector to be used may be processed, for example, by introducing gene that is expressed in the plant to produce a color-changeable enzyme or a luminous compound (GUS gene, GFP gene, luciferase gene etc.), an antibiotic marker with resistance (gentamicin marker, kanamycin marker etc.) or a marker gene for an anti-chemical reagent (e.g., anti-herbicide gene) and the like, for convenient identification and screening of a transgenic plant cell or plant.

Particularly, the above recombinant vector may be a recombinant vector obtained by inserting the above gene into a multiple cloning site of the expression vector 163-1300;

wherein, the construction method of the expression vector 163-1300 is: ligating a DNA band containing Double 35S promoter produced by cleaving enzymatically pJIT163 with KpnI and XhoI with a large fragment produced by cleaving enzymatically pCAMBIA1300 with KpnI and SalI to give the recombinant expression vector.

Another object of the present invention is to provide a method for breeding a transgenic plant with increased grain weight. The method for breeding a transgenic plant with increased grain weight provided by the present invention is: introducing the above gene into a target plant to give a transgenic plant with grain weight larger than that of the target plant.

Another object of the present invention is to provide a method for breeding a transgenic plant with increased grain length. The method for breeding a transgenic plant with increased grain length provided by the present invention is: introducing the above gene into a target plant to give a transgenic plant with grain length longer than that of the target plant.

Another object of the present invention is to provide a method for breeding a transgenic plant with increased grain number per panicle. The method for breeding a transgenic plant with increased grain number per panicle provided by the present invention is: introducing the above gene into a target plant to give a transgenic plant with larger grain number per panicle than that of the target plant.

Another object of the present invention is to provide a method for breeding a transgenic plant with rolled leaf. The method for breeding a transgenic plant with rolled leaf provided by the present invention is: introducing the above gene into a target plant to give a transgenic plant with rolled leaf.

The above gene is introduced into a target plant via the above recombinant vector. A plant expression vector bearing the OsXCL gene of the present invention may be transformed into a plant cell or tissue by Ti plasmid, Ri plasmid, plant virus vector, conventional biological methods, such as gene gun, pollen tube pathway, microinjection, electrical transformation, *Agrobacterium* mediation and so on.

The above plant may be a dicotyledonous plant or a monocotyledonous plant; the monocotyledonous plant is preferably rice, and the dicotyledonous plant may be *Arabidopsis thaliana*.

BEST MODE FOR CARRYING OUT THE INVENTION

The present invention will be further described with reference to the following specific Examples, which, however, are not intended to limit the present invention.

Each of the methods in the following examples is a conventional method, unless otherwise indicated.

EXAMPLE 1

Breeding of a Transgenic Rice Having Long, Large and Plural Grains and Rolled Leaf I. Construction of recombinant expression vector
 1. Cloning of OsXCL gene
 A pair of primers was artificially synthesized whose 5' terminals were added with NcoI and BamHI enzymatic cleavage sites respectively. The upstream primer and downstream primer are as follows:

(SEQ ID NO: 8)
F: 5'-CCATGG GAATCCAATCCACTCCACTCCACC-3' (30);

(SEQ ID NO: 9)
R: 5'-GGATCC CTAATAGGCGGTGTGGTGTTGCG-3 (29).

RNA, extracted from rice Pei'ai 64S (Chinese National Center for Rice Hybridization and Breeding, Changsha, China), was reversely transcribed to give the first chain of cDNA.

A PCR was performed to amplify cDNA as set forth by SEQ ID NO: 1 with the above upstream primer and downstream primer as primers and cDNA of rice Pei'ai 64S as a template. The PCR program started with a pre-denaturation at 94° C. for 5 min under a hot lid of 105° C., followed by 32 cycles of denaturation at 94° C. for 30s, annealing at 56° C. for 30s, extension at 72° C. for 1 min 20s, ended with a final extension at 72° C. for 10 min, and the temperature was maintained at 22° C.

The PCR system was:

| | |
|---|---|
| ddH$_2$O | 3.25 μl |
| 2×GC Buffer I | 12.5 μl |
| Primer-1(10 μM) | 2 μl |
| Primer-2(10 μM) | 2 μl |
| dNTP | 4 μl |
| Template cDNA | 1 μl |
| LA Taq polymerase | 0.25 μl |
| Total volume | 25 μl |

Figure 1:
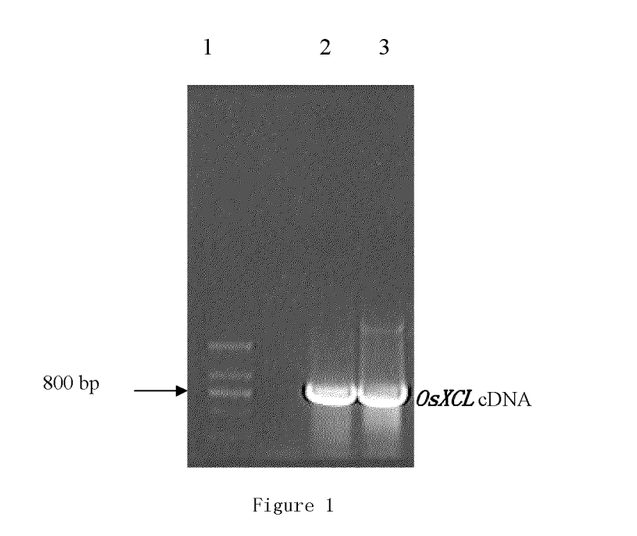
FIG. 1 shows the result of agarose gel electrophoresis of OsXCL cDNA amplified by PCR, wherein, lane 1 is a DNA marker; lanes 2 and 3 are OsXCL cDNA.

Agarose gel electrophoresis was performed with TAE electrophoresis buffer, and the resulting fragments of about 800 bp (FIG. 1) were designated as OsXCL.

The above OsXCL bands were recovered by a method of gel slug-press recovery using the kit of TIANGEN. The recovered fragments were linked into a pMD18-T vector (TA Cloning, Jinan TaiTianHe Biotechnology Limited Company), and the ligation system was as follows:

| | |
|---|---|
| Insert | 4.5 μl |
| T-Vector | 0.5 μl |
| Solution I | 5 μl |
| Total volume | 10 μl |

Figure 2:
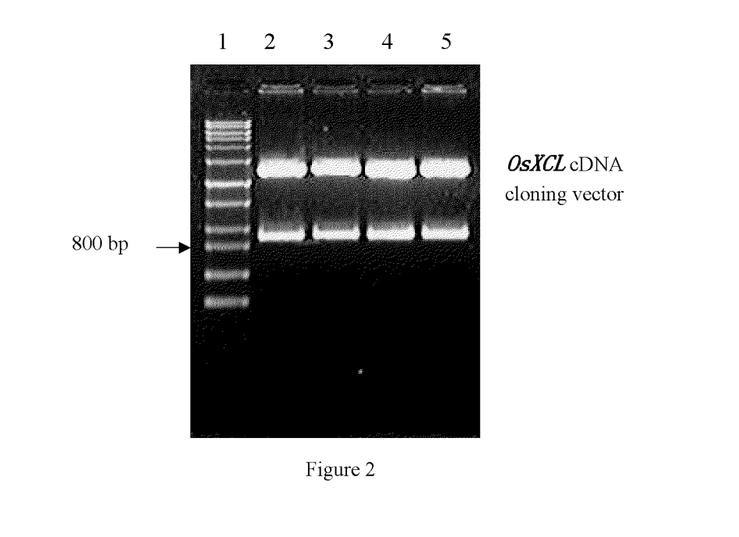
FIG. 2 is a confirmation figure of HindIII and EcoRI enzymatic cleavage after the ligation of OsXCL to T vector, wherein, lane 1 is a DNA marker; lanes 2-5 are EcoRI and HindIII double enzymatic cleavage results of the cloning vector of OsXCL cDNA.

The ligation lasted for 2 hours, and was transformed into competent cells of *E. coli* DH5a, spread on plates, and screened with ampicillin. Monoclones were chosen, from which plasmid was isolated and identified by double enzymatic cleavage with HindIII and EcoRI. Enzymatic cleavages indicated the presence of OsXCL bands of about 800 bp, as shown in FIG. 2.

Figure 3:
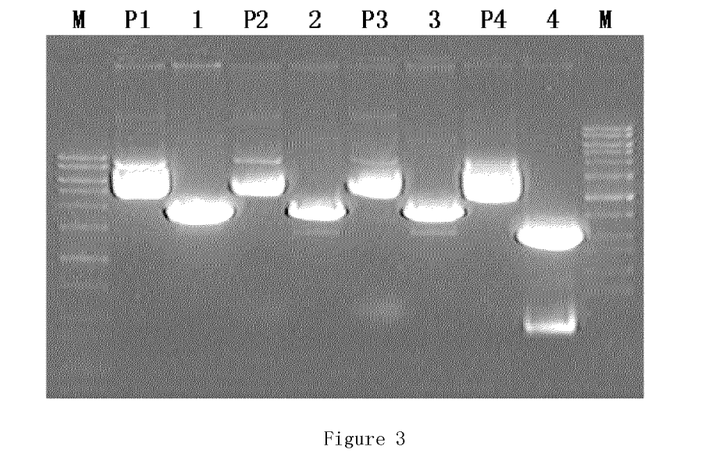
FIG. 3 is a confirmation figure of BamHI enzymatic cleavage after the ligation of OsXCL cDNA to T vector; P1, P2, P3 and P4 are bands of OsXCL cDNA plasmid before BamHI enzymatic cleavage; 1, 2, 3 and 4 are bands, of OsXCL cDNA plasmid after BamHI enzymatic cleavage, M is a DNA marker.

The plasmid was digested with BamHI to verify the direction in which the target fragment OsXCL was linked into a T vector, and the result, as shown in FIG. 3, was: since a BamHI site was added on the downstream primer, a inverse insertion into the T vector would result in a band of about 840 bp; in FIG. 3, P1, P2, P3 and P4 represent uncut plasmids, the band sizes of which are indicated by the 1 kb plus marker at right, and 1, 2, 3 and 4 represent post-cleavage results, the band sizes of which are indicated by the 1 kb plus marker at left. Comparing the results, it is indicated that except plasmid 4, each of plasmids 1, 2 and 3 was cut open, and the target fragments were linked forwardly (i.e., each is about 800 bp). The bacteria solutions corresponding to plasmids 1, 2 and 3 were sequenced, and the sequencing result suggested that the target fragment OsXCL has a sequence of positions 50-873 starting from the 5' end of SEQ ID NO: 1, and the ORF (Open reading frame) of OsXCL gene had a sequence completely identical with that as shown by positions 106 to 870 starting from the 5' end of SEQ ID NO: 1.

2. Construction of Recombinant Expression Vector

1) Construction of the Expression Vector 163-1300

Figure 4:
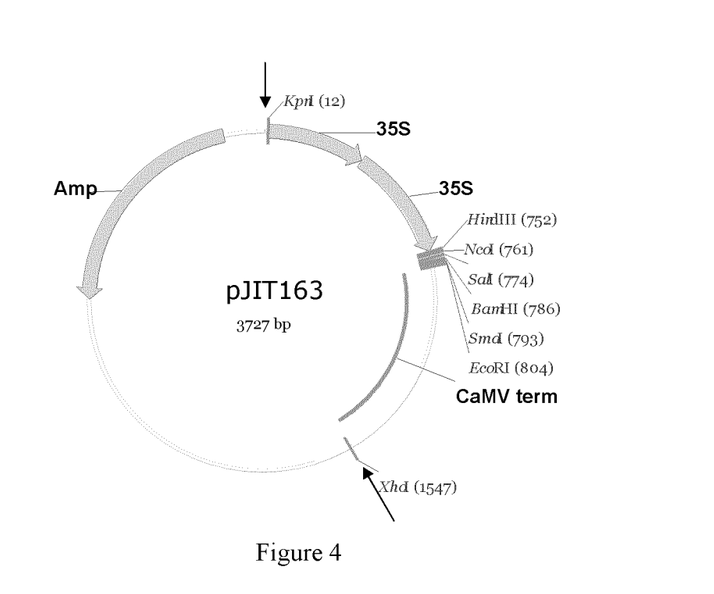
FIG. 4 is a map of pJIT163.
Figure 5:
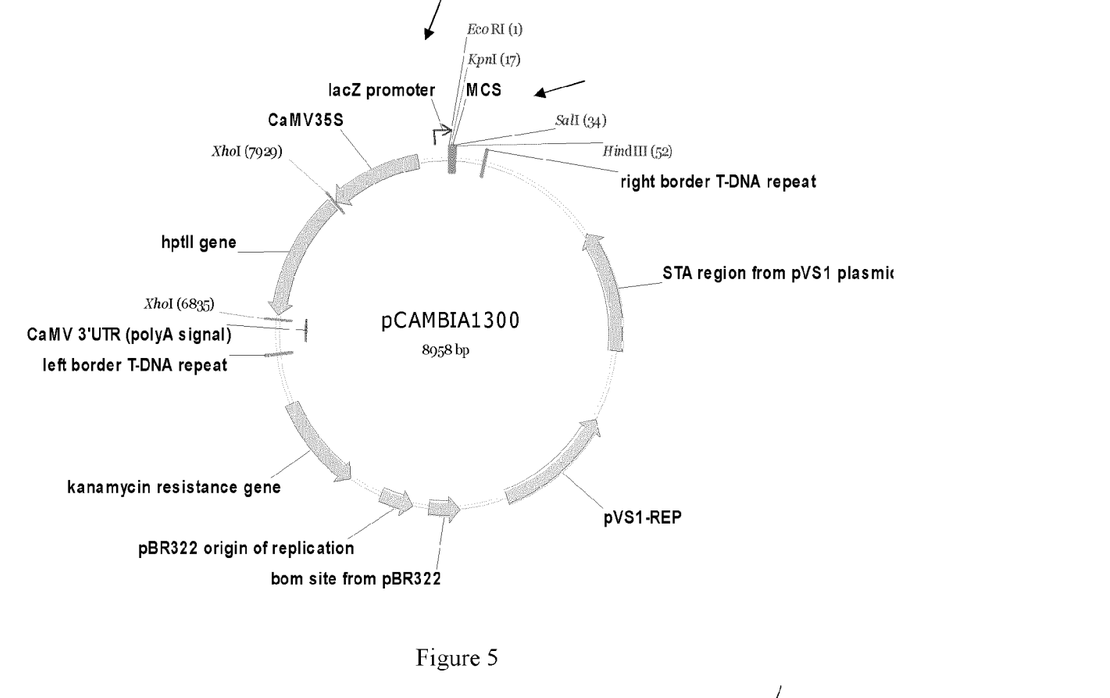
FIG. 5 is a map of pCAMBIA1300.

The pJIT163 (pGreen, www.pgreen.ac.uk) as shown in FIG. 4 was cleaved enzymatically with KpnI and XhoI, and the enzymatic cleavage results were identified via agarose gel electrophoresis prior to recovery of DNA bands containing Double 35S promoters. As to be shown in FIG. 5, pCAMBIA1300 (CambiaLabs, www.cambia.org/daisy/bioforge_legacy/3725.html) was cleaved enzymatically with KpnI and SalI, and large fragments were recovered. XhoI and SalI are isocaudarners. The two recovered fragments were ligated with T4 ligase overnight to construct a 163-1300 complex vector.

2) Construction of Recombinant Expression Vector

Figure 6:
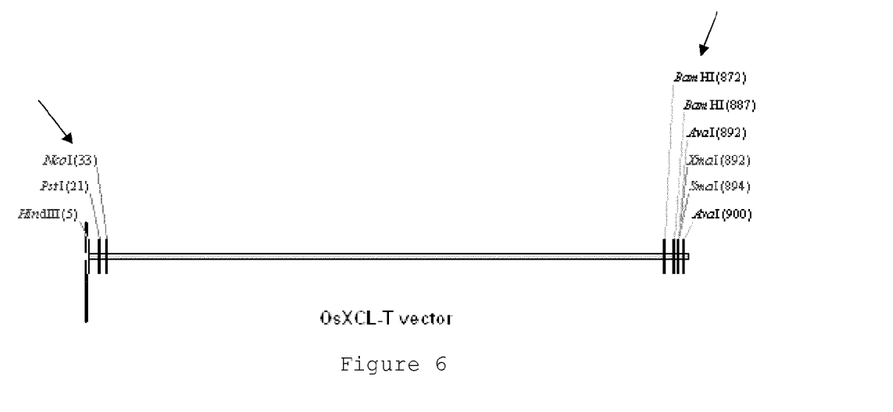
FIG. 6 is part of a map of a pMD18-T vector containing OsXCL.
Figure 7:
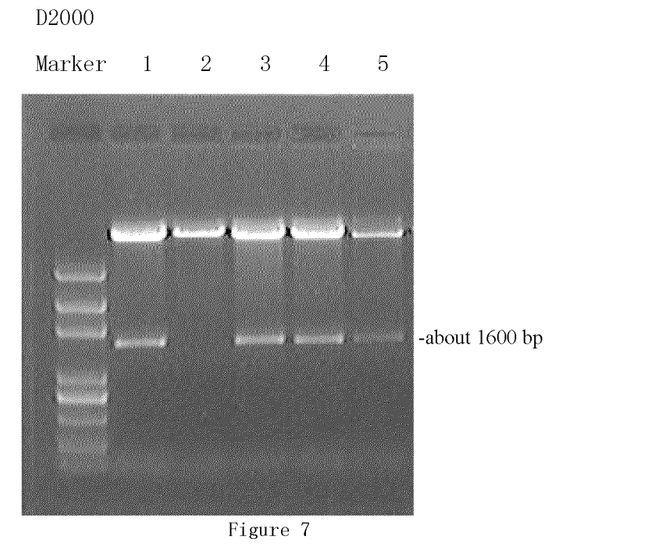
FIG. 7 is a confirmation figure of EcoRI enzymatic cleavage after the ligation of OsXCL to the expression vector; lanes 1-5 are enzyme enzymatic cleavage results of OsXCL expression vector enzymatically cleaved with EcoRI.
Figure 8:
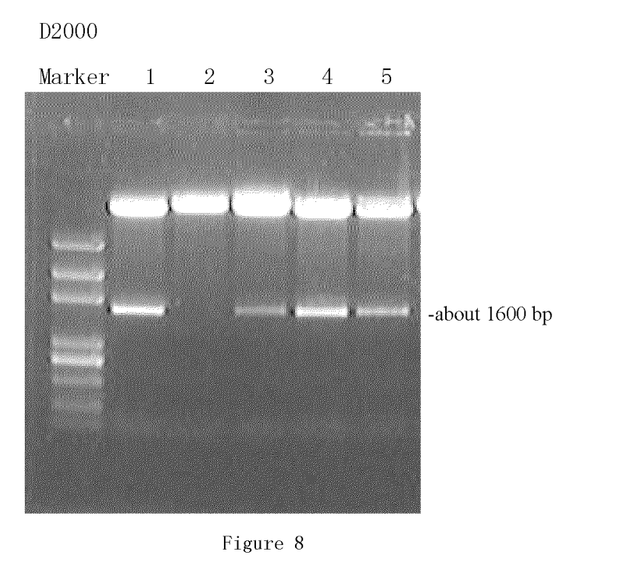
FIG. 8 is a confirmation figure of HindIII enzymatic cleavage after the ligation of OsXCL to the expression vector; lanes 1-5 are OsXCL expression vectors enzymatically cleaved with HindIII.

The T vector containing OsXCL, as shown in FIG. 6, was cut with enzymes NcoI and BamHI (whether BamHI acted on the enzymatic cleavage site introduced at position 872 through primer designing or the enzymatic cleavage site on T vector at position 887, the recovered fragments each contained the termination codon of OsXCL ORF). The expression vector 163-1300 was also cut with these two enzymes, recovered and then ligated, that is, the gene OsXCL was linked into the expression vector 163-1300, to construct a recombinant expression vector, designated as OsXCL-163-1300, which was confirmed by single enzymatic cleavage with HindIII and EcoRI, respectively. As shown in FIGS. 7 and 8 (1, 2, 3, 4 and 5 each represents bands of OsXCL expression vector after enzymatic cleavage), the results indicate that 1, 3, 4 and 5 each has a correct target band of about 1600 bp containing OsXCL.

Figure 9:
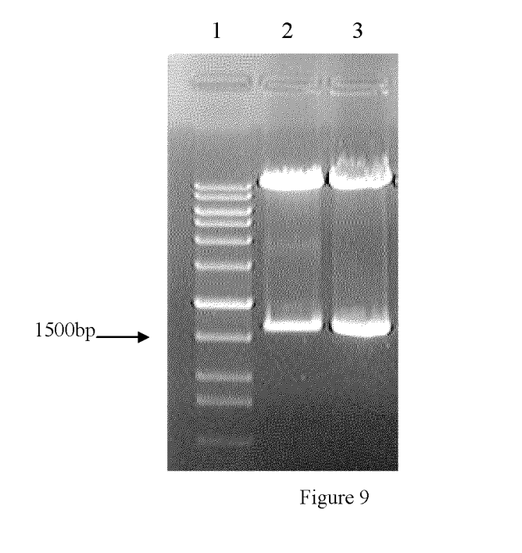
FIG. 9 is a confirmation figure of single enzymatic cleavage with EcoRI and HindIII respectively conducted on the plasmid isolated from *Agrobacterium*; lane 1, a DNA marker; lane 2, the result of OsXCL expression vector plasmid after enzymatic cleavage with EcoRI; lane 3, the result of OsXCL expression vector plasmid after enzymatic cleavage with HindIII.

II. Breeding and Detection of a Transgenic Rice Having Long Grain and Rolled Leaf 1. Obtaining of a Transgenic Rice Having Long, Large and Plural Grains and Rolled Leaf The recombinant expression vector of step 1.2 was used to transform *Agrobacterium* EHA105 (commercially available from Tiangen Biotech (Beijing) Co., Ltd.) with freeze-thaw method for transformation of *Agrobacterium*. Plasmids isolated from *Agrobacterium* were subjected to single enzymatic cleavage confirmation with EcoRI and HindIII respectively (FIG. 9). Wherein, the steps of freeze-thaw method for transformation of *Agrobacterium* were as follows:

wherein, the steps for freeze-thaw method were as follows: competent cells of *Agrobacterium* EHA105 stored at −70° C. were taken out and placed in an ice bath to thaw; 10-20 μl of pCAMBIA1300-2xCaMV35S-OsMsr1-CaMV35S-Term plasmid DNA (about 1-2 μg) was added into 200 ml of thawy competent cells of *Agrobacterium* stirred with a sterilized gun tip, and allowed to stand for several minutes; the mixture was placed in a liquid nitrogen for 1 min, and in a 37° C. water bath for 5 min, and then, 700-800 μl of LB liquid medium was added into, followed by oscillation under the temperature of 28° C. at 200 rpm for 4 h; centrifuged at 1000 g for 30 sec, part of the supernatant was discarded, with 100-150 μl left, which was resuspended by inhalation and ejection with a gun tip, and spread on a LB plate containing 50 mg/L Kanamycin, 50 mg/L Rifampicin and 34 mg/L chloromycetin; the plates were then placed invertly and cultivated at 28° C. for 2d.

The above confirmed recombinant *Agrobacterium tumefaciens* was used to infect callus tissues of rice 93-11 (Chinese National Center for Rice Hybridization and Breeding, Changsha, China) with the infection method. And then, infected calli were grown in a selection medium containing hygromycin (50 mg/L) to give a hygromycin-resistant regenerated plants.

Genomic DNA was extracted from leaves of the hygromycin-resistant regenerated plantls, and served as a template for PCR confirmation with the following primers designed based on hygromycin resistance gene:

(SEQ ID NO: 10)
pC13-hyg-F: 5'-ACCTGCCTGAAACCGAACTG-3';

(SEQ ID NO: 11)
pC13-hyg-R: 5'-CTGCTCCATACAAGCCAACC-3'.

Figure 10:
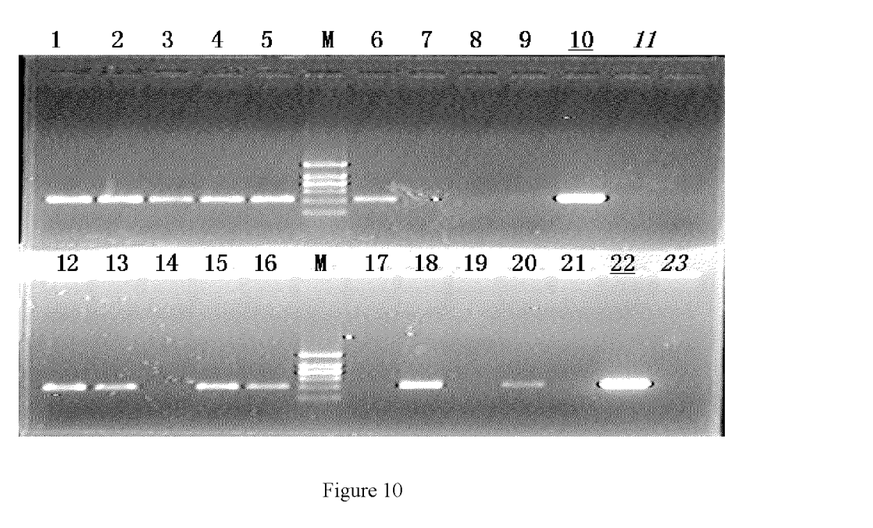
FIG. 10 is a confirmation figure of PCR conducted with the primers designed according to hygromycin resistance gene. Wherein, M is a DNA marker; lanes 1-9 and 12-21, PCR results of hygromycin resistance gene conducted with the genomic DNA of OsXCL transgenic rice plant as a template; lanes 10 and 22, the hygromycin enzyme resistance gene amplified with the expression vector plasmid as a template was used as the positive control; lanes 11 and 23, template free (water) negative control.

The confirmation results are shown in FIG. 10, target bands were obtained in 1, 2, 3, 4, 5, 6, 12, 13, 15, 16, 18 and 20, 12 plant lines in total, that is, there were totally 12 positive plants in T0 generation of the transgenic plants (the hygromycin gene closely linked with OsXCL had been integrated into the rice genome).

2. Detection Analysis

The above OsXCL transgenic rice was transferred into a greenhouse for cultivation, bagged and self-crossed, and seeds from transgenic rice were collected.

Meanwhile, the transgenic rice of expression vector 163-1300 free of OsXCL gene was used as an empty vector control; and the non transgenic rice was also used as a control.

1) Quantitative PCR Detection

Figure 11:
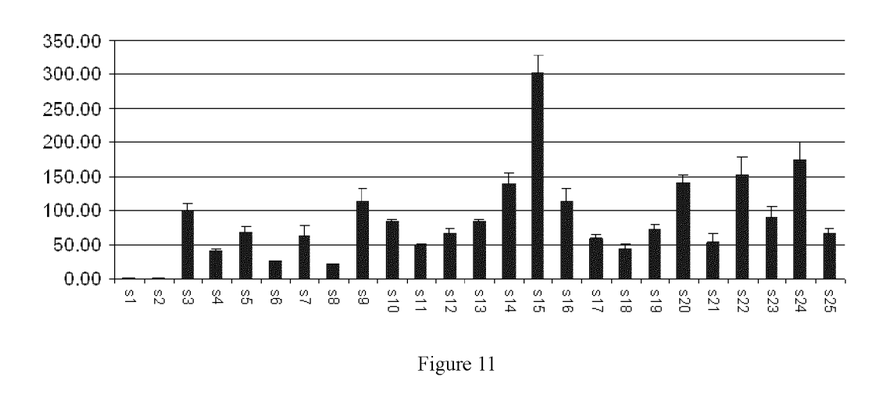
FIG. 11 is a relative expression analysis of quantitative real-time PCR conducted on a T0 93-11 plant transformed with gene Os XCL. S1, a non-transgenic control rice; S2, a control rice with empty vector free of gene OsXCL; S3-S25, T0 93-11 rice plants transformed with gene OsXCL.

Quantitative PCR detection was performed on OsXCL transgenic rice and non transgenic rice with DNA sequence primers 108-F and 108-R of OsXCL gene; the results are shown in FIG. 11, OsXCL had a relative low expression level in non transgenic rice 93-11, and a dramatically improved expression level in OsXCL transgenic rice.

Wherein, primers for RT-PCR were as follows:

(SEQ ID NO: 12)
108-F: 5'-CCGCCATCATCCAAACTGA-3'(Tm 59, PCR 56);

(SEQ ID NO: 13)
108-R: 5'-GGTGACCACGCCCTTCTTC-3'(Tm 59, PCR 56).

RT-PCR System

| Reagent | Concentration | Volume (ul) +RT | Volume (ul) −RT | Final concentration (uM) |
| --- | --- | --- | --- | --- |
| 2x Master reaction solution | 2x | 5.0 | 5.0 | 1x |
| QuantutyTec RT mix | 100x | 0.1 | 0.0 | |
| 108-F primer | 20.0 uM | 0.2 | 0.2 | 0.4 |
| 108-R primer | 20.0 uM | 0.2 | 0.2 | 0.4 |
| RNA-free water | | 0.5 | 0.6 | |
| Template RNA | 5 ng/ul | 4.0 | 4.0 | 20 ng/reaction |
| Total | | 10.0 | 10.0 | |

| Number of cycles for PCR | melting curve conditions |
| --- | --- |
| 48° C./30 min, 1 cycle | 95° C./15 sec |
| 95° C./10 min, 1 cycle | 60° C./20 sec |
| 95° C./15 sec, 56° C./1 min, 40 cycles | 95° C./15 sec |

2) Phenotype Observation and Statistics

A. Seeds from T0 plants of the OsXCL gene transgenic rice 93-11, empty vector control and non-transgenic rice 93-11 were weighted and measured for hundred-grain-weight and grain length, and the T0 plants were observed and counted for number of plants having rolled leaves.

Figure 12:
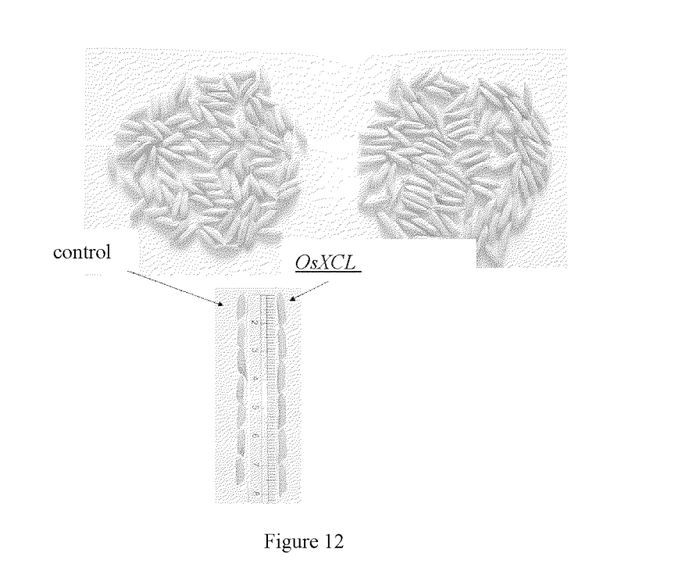
FIG. 12 are pictures of grains of OsXCL trans genic rice and control grains.

The trial was repeated three times, and the results are shown in FIG. 12 and Table 2. Comparing with non transgenic rice 93-11 and empty vector control, the OsXCL transgenic rice was significantly rised in hundred-grain-weight and grain length. Wherein, as compared with the wild-type rice, the hundred-grain-weight of OsXCL transgenic rice was increased by 25.1% in fresh weight and 23% in dry weight, the grain length was increased by ¼, and the chalky grain rate was decreased (improved in rice quality).

TABLE 2

Hundred-grain-weight and grain length of seeds from T0 plants

|  | OsXCL transgenic rice | Empty vector control | Non-transgenic rice |
|---|---|---|---|
| Grain length (mm) | 11.3833 ± 0.08868 | 8.7027 ± 0.08997 | 8.6167 ± 0.07836 |
| Hundred-grain-weight (fresh weight) (g) | 4.224 ± 0.11 | 3.401 ± 0.08 | 3.377 ± 0.10 |
| Hundred-grain-weight (dry weight) (g) | 3.36 ± 0.09 | 2.761 ± 0.07 | 2.73 ± 0.09 |

Note:
dry weight of seeds was obtained by placing the seeds at 37° C. for 3 days prior to weighting them.

Figure 13:
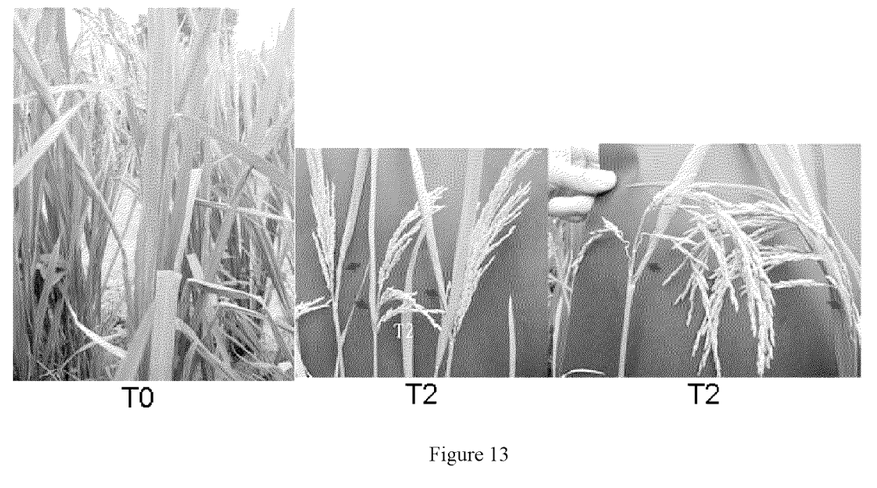
FIG. 13 are pictures of OsXCL transgenic T0 generation rice with leaves rolled up and T2 generation rice with the flag leaf bases curled at late stage.

Comparing with non-transgenic rice and empty vector control, T0 plants of the OsXCL transgenic rice has a slightly broader leaf and a significantly rolled flag leaf (FIG. 13). Plants involving rolled leaves comprise up to 90% of the OsXCL transgenic rice plants. Curls start from leaf bases and, at late development stage, upper portions of the leaves expand.

B. Grain number per panicle of $T_2$ plant lines overexpressing OsXCL gene and control plant lines transformed with pCAMBIA1300-163 empty vector were counted, and number of $T_2$ plants having rolled leaves was observed.

Figure 14:
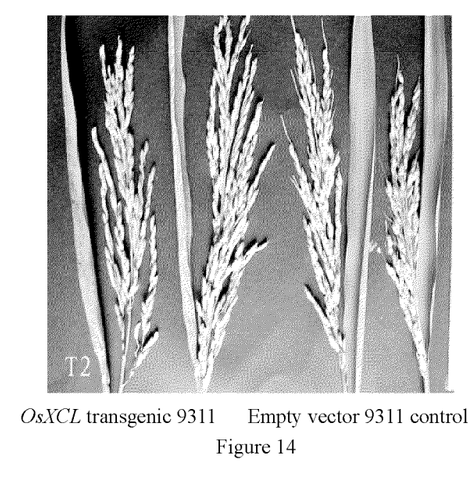
FIG. 14 is a picture showing increased grain number per panicle of T2 generation of the transgenic 9311 rice overexpressing OsXCL gene.

The trial was repeated three times. FIG. 14 and Table 3 show the grain number per panicle. Comparing with the empty vector control, the transgenic 9311 rice overexpressing OsXCL gene was significantly increased in grain number per panicle.

C. Thirty grains were chosen from $T_3$ plant lines overexpressing OsXCL gene and control plant lines transformed with pCAMBIA1300-163 empty vector, respectively, and measured in grain length.

Figure 15:
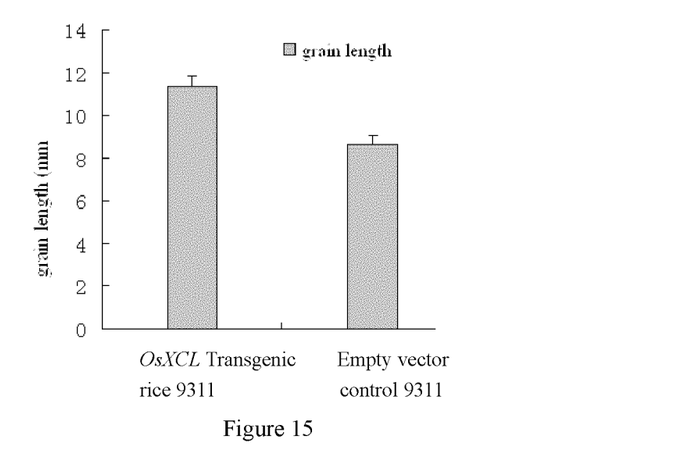
FIG. 15 is a graph showing grain growth of the transgenic 9311 rice overexpressing OsXCL gene.

The trial was repeated three times, and the results are shown in FIG. 15. Empty vector control plant lines had an average grain length of 8.62 mm; plant lines overexpressing OsXCL gene had a grain length of 11.38 mm, 24.30% longer than that of the seeds of the empty vector control plant lines.

Accordingly, all the transgenic plant lines overexpressing OsXCL gene exhibit a phenotype of increased grain length and grain weight from T0 generation to T3 generation.

EXAMPLE 2

Breeding of Transgenic *Arabidopsis thaliana*

A recombinant expression vector OsXCL-163-1300 was obtained according to the method provided in Example 1, and then integrated into the genome of *Arabidopsis thaliana* (Col-0, commercially available from *Arabidopsis* Biological Resource Center, ABRC) through floral-dip method mediated by *Agrobacterium*; screening was performed on a MS medium containing hygromycin (50 mg/l), seeds from T2 generation were continuously screened on the MS containing hygromycin, and plant lines with the segregation ratio being 3:1 were chosen for continuous screening in T3 generation; if 100% of the seeds from T3 generation may grow on a MS containing hygromycin, this plant line was deemed as homozygous line, and a transgenic *Arabidopsis thaliana* overexpressing OsXCL gene was obtained.

Meanwhile, *Arabidopsis thaliana* transformed with expression vector 163-1300 free of OsXCL gene was used as an empty vector control.

Figure 16:
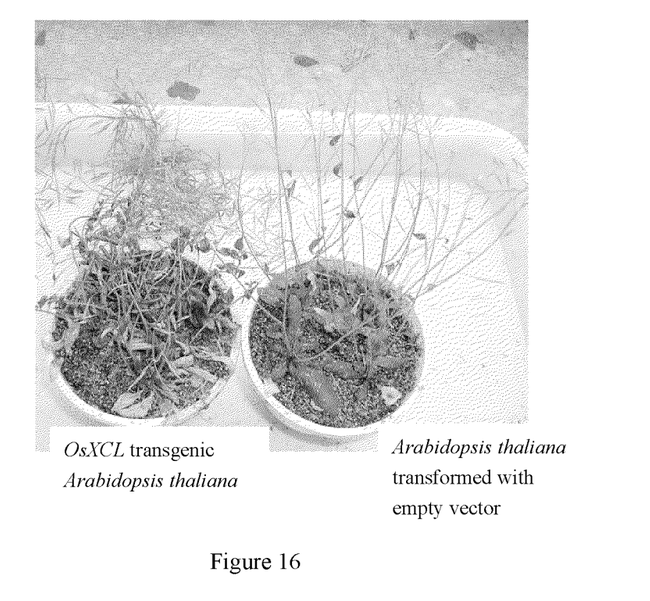
FIG. 16 is a picture showing the transgenic *Arabidopsis thaliana* overexpressing OsXCL gene with dramatically increased siliques and leaves curled.

The T3 generation of transgenic *Arabidopsis thaliana* overexpressing OsXCL gene and the empty vector control were breeded, and silique number and leaf curls were counted. The results are shown in FIG. 16, the transgenic *Arabidopsis thaliana* overexpressing OsXCL gene had dramatically increased siliques and its leaves curled.

INDUSTRIAL APPLICATION

The OsXCL transgenic rice bred by the present invention has a hundred-grain-weight up to 4.224 g, as compared with the wild-type control, has an increase by 25.1% in weight,

TABLE 3 increase in grain number per panicle of the transgenic 9311 rice overexpressing OsXCL gene

| | Panicle-1 | Panicle-2 | Panicle-3 | Panicle-4 | Panicle-5 | Panicle-6 | Panicle-7 | Panicle-8 | Panicle-9 | Panicle-10 | Total grain number | Grain number per panicle | Increase % |
|---|---|---|---|---|---|---|---|---|---|---|---|---|---|
| Transformed with OsXCL 9311* | 213 | 183 | 215 | 268 | 191 | 234 | 188 | 258 | 244 | 261 | 2255 | 225.5 | 11.0 |
| Transformed with empty vector 9311 | 190 | 195 | 220 | 187 | 201 | 221 | 204 | 196 | 223 | 195 | 2032 | 203.2 | |

*Transgenic plant line C3-3

FIG. 13 shows results of leaf curls. The flag leaf bases of the transgenic 9311 rice overexpressing OsXCL gene were curled at late stage.

an increase by ¼ in grain length and an increase by 11% in grain number per panicle. OsXCL was overexpressed in rice, causing leaf curls in rice and significant increase in grain length and thousand-grain-weight as well as improvement in rice quality and grain number per panicle. The application of OsXCL can not only increase production, but also improve the quality of rice; moreover, it has no negative impact on rice growth and development. Therefore, this gene is a considerably ideal gene for improving crops, such as rice etc. by biotechnology and genetic engineering, and will play an active in safe production of rice and other crops.

What is claimed is:

1. A method for increasing one or more of grain weight, grain length, grain number per panicle and/or rolled leaves of a plant, which comprises:
   introducing a recombinant expression vector comprising a nucleic acid encoding the protein as set forth by SEQ ID NO. 2 into a target plant;
   screening the transgenic plant for the recombinant expression vector; and
   breeding the transgenic plant wherein the plant exhibits increased grain weight, increased grain length, increased grain number per panicle and/or rolled leaves compared to a non-transgenic plant.

2. The method according to claim 1, wherein the plant is a dicotyledonous plant or a monocotyledonous plant.

3. A method for increasing one or more of grain weight, grain length, grain number per panicle and/or rolled leaves of a plant, comprising:
   regenerating a transgenic cell line or breeding a recombinant plant with another plant in a selection medium to obtain a transgenic plant, wherein the cell line or recombinant plant comprises a heterologous nucleic acid selected from
   a) a nucleic acid encoding the polypeptide that is encoded by nucleotides 106-870 of SEQ ID NO. 1;
   b) a nucleic acid encoding the polypeptide that is encoded by nucleotides 50-873 of SEQ ID NO. 1; and
   selecting and growing a plant with increased grain weight, increased grain length, increased grain number per panicle and/or rolled leaves of the transgenic plant with compared to a non-transgenic plant.

4. A method for increasing one or more of grain weight, grain length, grain number per panicle and/or rolled leaves of a plant, which comprises:
   introducing a recombinant expression vector comprising a nucleic acid selected from:
   a) a nucleic acid encoding the polypeptide that is encoded by positions 106-870 from the 5' end of SEQ ID NO. 1;
   b) a nucleic acid encoding the polypeptide that is encoded by positions 50-873 from the 5' end of SEQ ID NO. 1;
   into a target plant;
   screening the transgenic plant for the recombinant expression vector; and identifying and breeding the transgenic plant wherein the plant exhibits increased grain weight, increased grain length, increased grain number per panicle and/or rolled leaves compared to a non-transgenic plant.

5. The method according to claim 4, wherein the plant is a dicotyledonous plant or a monocotyledonous plant.

6. The method according to claim 4, wherein the recombinant expression vector is obtained by:
   inserting the nucleic acid into a multiple cloning site of the expression vector 163-1300;
   wherein, the construction method of the expression vector 163-1300 is: ligating a DNA band containing Double 35S promoter produced by cleaving enzymatically pJIT 163 with Kpnl and Xhol with a large fragment produced by cleaving enzymatically pCAMBIA1300 with Kpnl and Sail to give the recombinant expression vector;
   transforming the recombinant expression vector into a host cell; and
   identifying and recovering the recombinant vector with the inserted nucleic acid.

7. The method according to claim 1, wherein the recombinant expression vector is obtained by:
   inserting the nucleic acid into a multiple cloning site of the expression vector 163-1300;
   wherein, the construction method of the expression vector 163-1300 is: ligating a DNA band containing Double 35S promoter produced by cleaving enzymatically pJIT 163 with Kpnl and Xhol with a large fragment produced by cleaving enzymatically pCAMBIA1300 with Kpnl and Sail to give the recombinant expression vector,
   transforming the recombinant expression vector into a host cell; and
   identifying and recovering the recombinant vector with the inserted nucleic acid.

8. The method according to claim 2, wherein the a dicotyledonous plant is *Arabidopsis thaliana*, and the a monocotyledonous plant is rice.

9. The method according to claim 5, wherein the a dicotyledonous plant is *Arabidopsis thaliana*, and the a monocotyledonous plant is rice.

* * * * *